US00PP28946P2

(12) United States Plant Patent
O'Connell

(10) Patent No.: US PP28,946 P2
(45) Date of Patent: Feb. 6, 2018

(54) ***ECHINOPSIS* PLANT NAMED 'FLAMBEAU'**

(50) Latin Name: *Echinopsis hybrida*
Varietal Denomination: Flambeau

(71) Applicant: Renee O'Connell, Escondido, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/330,625

(22) Filed: Oct. 18, 2016

(51) Int. Cl.
*A01H 5/02* (2006.01)

(52) U.S. Cl.
USPC ..... Plt./372

(58) Field of Classification Search
USPC ..... Plt./372
See application file for complete search history.

*Primary Examiner* — Annette H Para
(74) *Attorney, Agent, or Firm* — Cassandra Bright

(57) ABSTRACT

A new and distinct *Echinopsis* cultivar named 'Flambeau' is disclosed, characterized by distinctive magenta and orange flowers in a triple whorl produced over a 6 to 7 month period. Plants are fast growing and very free offsetting, resulting in both improved propagation rates and improved finished plant production times. *Echinopsis* is an ornamental cactus, useful as an indoor ornamental plant and outdoors in warm climates.

3 Drawing Sheets

Latin name of the genus and species: *Echinopsis hybrida*.
Variety denomination: 'FLAMBEAU'.

BACKGROUND OF THE INVENTION

The new cultivar, *Echinopsis* 'Flambeau', was found by the inventor, Renee O'Connell, as the result of a crossing made April 2013 as part of a planned breeding program. The seed parent variety is the unpatented proprietary variety referred to as *Echinopsis hybrida* 'RQ 17', a member of the Chamaelobivia group of *Echnopsis*. The pollen parent is the unpatented proprietary variety *Echinopsis hybrida* 'KK 03', also a member of the Chamaelobivia group. *Echinopsis* 'Flambeau' was selected by the inventor, Renee O Connell, in May of 2014 from a group of seedlings resulting from the 2013 crossing, at a commercial greenhouse in Vista. Calif.

Asexual reproduction of the new cultivar 'Flambeau' was first performed in Vista, Calif., at a commercial greenhouse, by vegetative offsets, known as "peanuts" in May of 2014. 'Flambeau' has since produced multiple generations and has shown that the unique features of this cultivar are stable and reproduced true to type.

SUMMARY OF THE INVENTION

The cultivar 'FLAMBEAU' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FLAMBEAU' These characteristics in combination distinguish 'FLAMBEAU' as a new and distinct *Echinopsis* cultivar:

1. 'Flambeau' is very freely offsetting, producing 100 to over 150 offsets in a 1 gallon pot.
2. 'Flambeau' is very floriferous, often producing over 150 flowers a season when grown in a 1 gallon pot.

3. 'Flambeau' flowers for a 6-7 month span whereas comparable *Echinopsis* hybrids do not.
4. During the 6-7 month span of flowering, the new variety also displays 2 or more heavy "flushes" of flowers; at times there may be 35 to 40 flowers open at the same time when grown in a 1 gallon pot.
5. Distinctive flower; magenta petals, with a reddish-orange underside, surrounded by decorative sepals colored magenta and orange.
5. Flowers typically 2 inches in diameter, occurring in multiple whorls, giving the appearance of a double flower.
6. 'Flambeau' is fast growing, forming an offsetting plant ready for sale in a 9 cm pot within 4-5 months from a single "peanut". Two full sized 9 cm plants will fill a 1 gallon pot in 2 months from transplant, ready for sale.

Plants of the new cultivar 'FLAMBEAU' are similar to plants of the seed parent, in most horticultural characteristics, however, plants of the new cultivar 'FLAMBEAU' differ in the following;

1. 'Flambeau' produces flowers with underside of petals a contrasting color, whereas 'RQ 17' produces flowers of one color.
2. 'Flambeau' produces thicker apical spines than *Echinopsis* hybrid 'RQ 17'.
3. 'Flambeau' is more floriferous than *Echinopsis* hybrid 'RQ 17'.
4. 'Flambeau' produces more offsets than *Echinopsis* hybrid 'RQ 17'.
5. The flowers of 'Flambeau', have more petals per flower, than those of *Echinopsis* hybrid 'RQ 17'.

Plants of the new cultivar 'FLAMBEAU' are similar to plants of the pollen parent, in most horticultural characteristics, however, plants of the new cultivar 'FLAMBEAU' differ in the following;

1. 'Flambeau' has larger flowers than *Echinopsis* hybrid 'KK 03'.

2. 'Flambeau' is more resistant to the pathogen *Bipolaris cactivora* (*Helminthosporium cactivorum*) than is *Echinopsis* hybrid 'KK 03'
3. The flowers of *Echinopsis* hybrid 'Flambeau', due to the extra petals per flower, are more double-flowered than those of *Echinopsis* hybrid 'KK 03'.
4. The flowers of the *Echinopsis* hybrid 'Flambeau' have at least two colors, whereas the flowers of the *Echinopsis* hybrid 'KK 03' are one color.
5. The flowers of the 'Flambeau' can occur in several, very heavy flushes of flowers over a long span of flowering of 6-7 months, whereas the flowers of the *Echinopsis* hybrid 'KK 03' occur in less heavy flushes, and the flowering span is only 3 months.

COMMERCIAL COMPARISON

Plants of the new cultivar 'FLAMBEAU' are comparable to the unpatented, commercial variety *Echinopsis* 'Fire Chief'. The two *Echinopsis* varieties are similar in most horticultural characteristics; however, the new variety 'FLAMBEAU' differs in the following:

1. *Echinopsis* hybrid 'Flambeau' produces flowers with at least two colors, whereas those of *Echinopsis* hybrid 'Fire Chief' are a monotone orange.
2. *Echinopsis* hybrid 'Flambeau' produces many more offsets than does *Echinopsis* hybrid 'Fire Chief', aiding in faster production of plants for commercial sales.
3. *Echinopsis* hybrid 'Flambeau' grows faster than does *Echinopsis* hybrid 'Fire Chief', accelerating production times in the commercial nursery.
4. The flower size of *Echinopsis* hybrid 'Flambeau' is larger than the flower size of *Echinopsis* 'Fire Chief'
5. *Echinopsis* hybrid 'Flambeau' exhibits several heavy flushes of flowers over a 6 to 7 month flowering span, whereas *Echinopsis* hybrid 'Fire Chief' does not produce these flower flushes, and the flowering span is only 1-2 months.

Plants of the new cultivar 'FLAMBEAU' can also be comparable to the unpatented commercial variety *Echinopsis* 'Westfield Alba'. The two *Echinopsis* varieties are similar in most horticultural characteristics; however, the new variety 'FLAMBEAU' differs in the following:

1. *Echinopsis* hybrid 'Flambeau' produces much larger "peanuts" (vegetative offsets) than does *Echinopsis* 'Westfield Alba', aiding in producing a saleable plant faster.
2. *Echinopsis* hybrid 'Flambeau' grows at a faster rate than does *Echinopsis* hybrid 'Westfield Alba', thereby enhancing production and reducing production time.
3. *Echinopsis* hybrid 'Flambeau' grows with a more upright morphology, unlike the prostrate, pendulous habit of *Echinopsis* hybrid 'Westfield Alba'.
4. *Echinopsis* hybrid 'Flambeau' produces flowers with at least 2 colors, whereas *Echinopsis* hybrid 'Westfield Alba' has monotone white flowers.
5. The flowers of *Echinopsis* hybrid 'Flambeau' are much larger than those of *Echinopsis* hybrid 'Westfield Alba'.

BRIEF DESCRIPTION OF THE PHOTOGRAPHS

The accompanying photographs illustrate in full color typical of plants of *Echinopsis* 'Flambeau' grown in a greenhouse in Vista, Calif. Age of the plant photographed is approximately 5 months from a vegetative offset, "peanut". The photographs were taken using conventional techniques and although colors may appear different from actual colors due to light reflectance it is as accurate as possible by conventional photographic techniques. All photographs provided by the breeder.

DETAILED BOTANICAL DESCRIPTION

Figure 1:
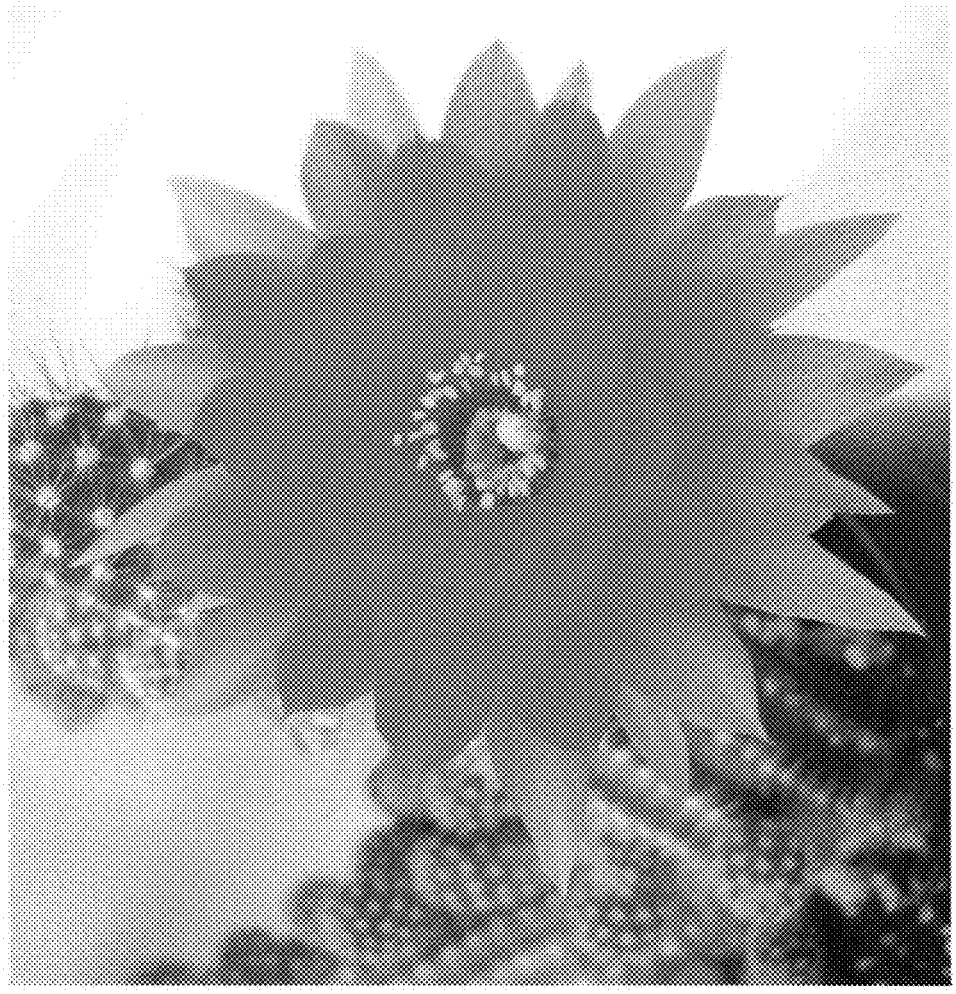
FIG. 1 illustrates in full color in close-up of the flower of *Echinopsis* hybrid 'Flambeau', grown in a greenhouse (approximately 3000 to 4000 foot candles) in Vista, Calif.
Figure 2:
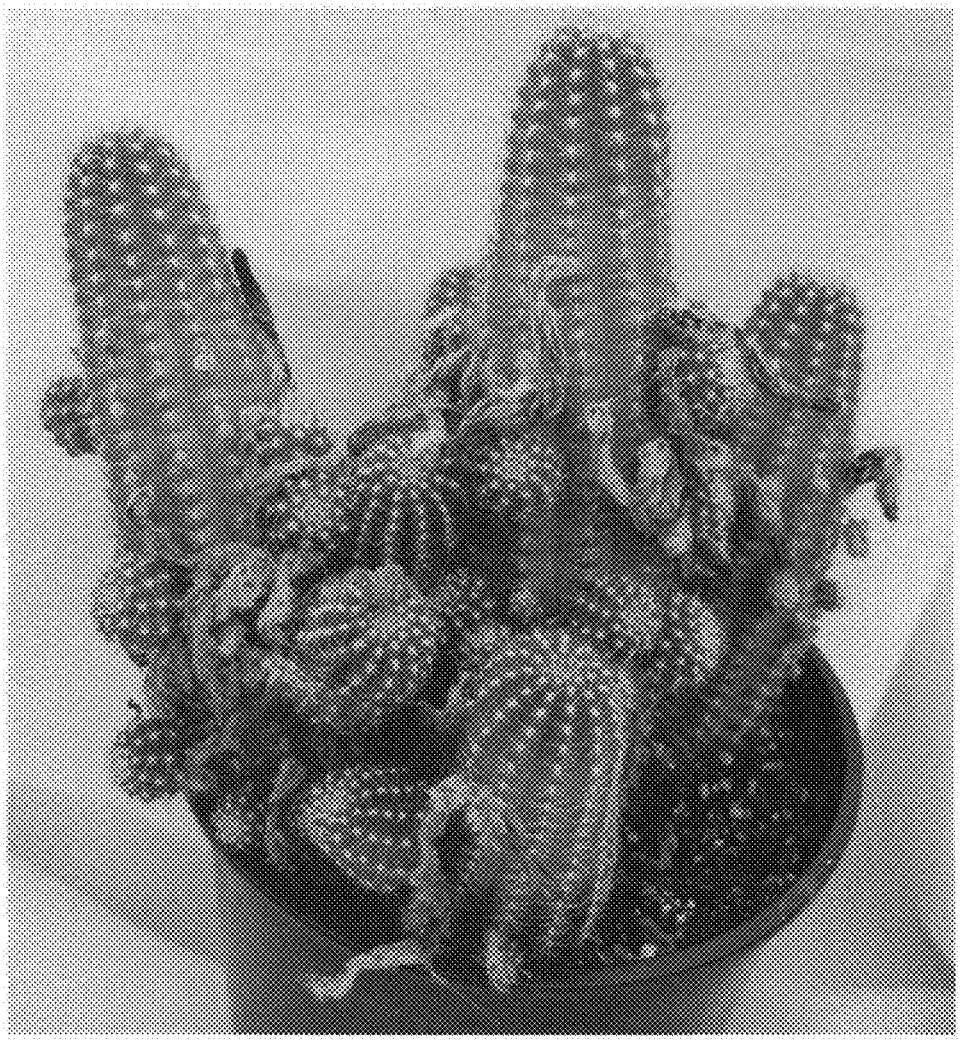
FIG. 2 illustrates in full color *Echinopsis* hybrid 'Flambeau' in 1 gallon pot with spent flowers.
Figure 3:
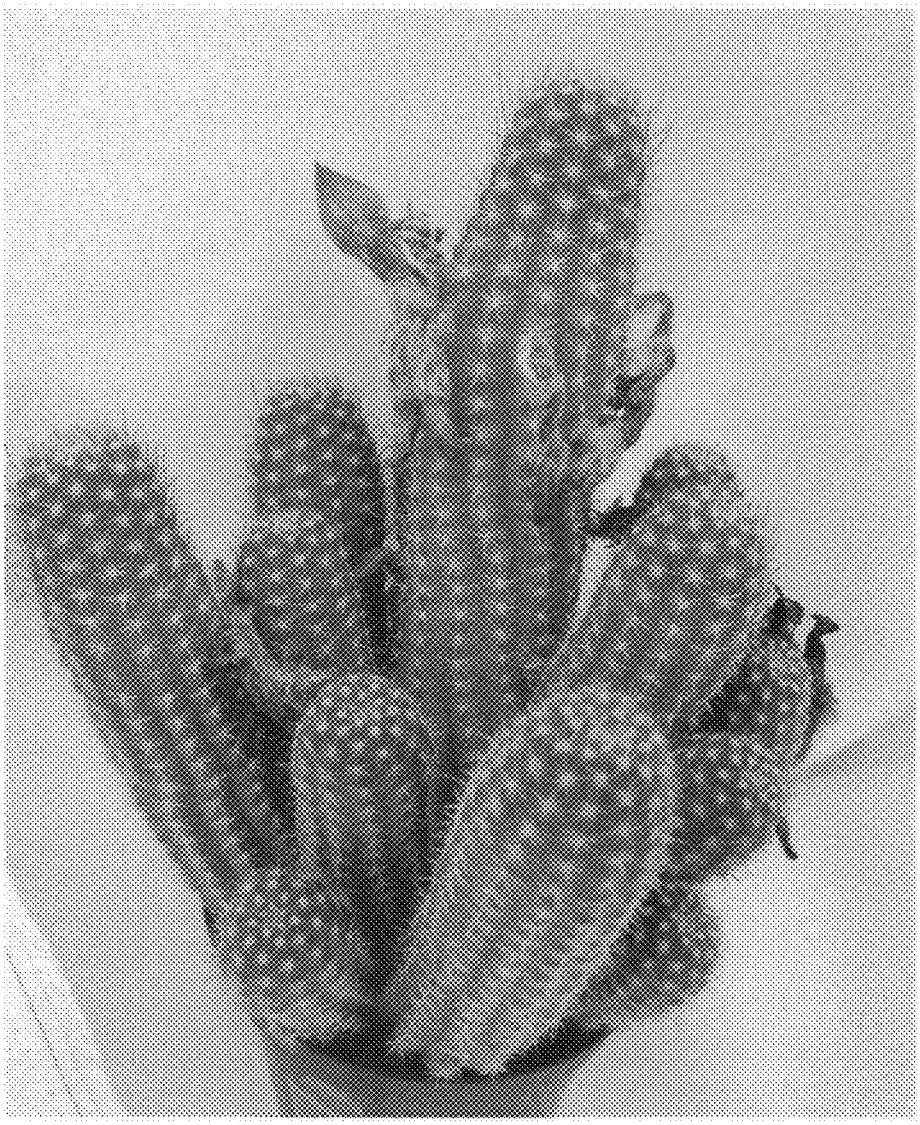
FIG. 3 illustrates in full color the plant morphology of *Echinopsis* hybrid 'Flambeau'

In the following description, color references are made to The Royal Horticultural Society Colour Chart, 2007, except where general terms of ordinary dictionary significance are used. The following observations and measurements describe 'Flambeau' plants in a commercial shadehouse in Vista, Calif. Temperatures ranged from 34° F. to 90° F. night and day. No artificial light, photoperiodic treatments or chemical treatments were given to the plants. Natural light conditions were approximately 2500-4000 foot candles of light. Measurements and numerical values represent averages of typical plant types.

Botanical classification: *Echinopsis hybrida* 'FLAMBEAU'.

PROPAGATION

Type of propagation typically used: Vegetative offsets known as "peanuts".

Time to initiate roots: About 3 weeks at approximately 22° to 26° C.

Root description: Densely fibrous.

PLANT

Age of plant described: Approximately 4 months.

Container size of the plant described: 9 cm.

General plant description: Columnar, clump forming small cactus.

Growth habit: Upright, becoming prostrate with maturity. Abundant offsets forming clumps from base.

Plant height: Approximately 9 to 17 cm.

Quantity of offsets: 2 to 10 present on a 4 inch pot, at the end of the growing season, in September.

Stem description:

*Diameter.*—3.5 to 4.0 cm.

*Length.*—12 to 17 cm.

*Color.*—Near RHS Green 138B and 138C.

Areole:

*Spacing.*—Approximately 4 mm apart on rib.

*Quantity.*—Approximately 500 per mature stem.

Spine/thorn description:

*Arrangement.*—Spines radially arranged. Average 10 ribs of spines vertically linear, nearly straight, very minor spiral. Ribs spaced approximately 10 to 15 mm apart. No prominent central spine. Radial spines approximately 4 mm, colored near Greyed-Yellow 161D. Moderate quantity of dense trichomes approximately 1 mm colored near Greyed-Yellow 161C.

FLOWER

Natural flowering season: Approximately Spring until Fall in Southern California. Flowers constantly present, with 2 or more flushes of abundant flowering occurring.

Inflorescence type and habit: Open funnel form. Reduced tube length open, radial flower of multiple whorls.
Flower longevity on plant: 1 to 2 days.
Quantity of flowers: 4 inch pot has approximately 5 to 15 flowers and buds. A mature plant in a 1 gallon pot can have 35 to 40 flowers during peak flowering.
Individual flower size:
*Diameter.*—8 cm.
*Length.*—4 cm.
*Flower tube length.*—2.5 cm.
*Flower tube diameter at distal end.*—1.7 cm.
*Flower tube diameter at proximal end.*—0.9 cm.
Petals:
*Petal arrangement.*—Triple whorl.
*Length.*—Average range 2.5 to 3.5 cm.
*Width.*—0.7 cm.
*Quantity.*—Typically 25 to 35.
*Texture.*—Glabrous all surfaces.
*Appearance.*—Very shiny upper surface, moderately shiny lower surface.
*Margin.*—Entire.
*Tip shape.*—Mucronate.
Color:
*Petals.*—When opening: Upper surface: Near RHS Red 53D, but much brighter. Lower surface: Near RHS Red 53B. Fully opened: Upper surface: Between Red 46C and Red-Purple N57A, but much brighter. Faint streaking near Orange-Red 32A. Lower Surface: Brighter than RHS Red 53C, streaked Orange-Red 32D. Fading: Upper Surface: Near Red 53D, streaks of Orange-Red 33C. Lower Surface: Near Red 53D, streaks of Orange-Red 33C.
Flower tube:
*Inner surface.*—Near RHS Red 47B.
*Outer surface.*—Near RHS Orange-White 159A.
Bud:
*Shape.*—Oblong.
*Length.*—Approximately 7 cm.
*Diameter.*—Approximately 3.0 cm
*Color.*—Near RHS Orange-Red 32D.
Peduncle:
*Length.*—2.0 cm.
*Diameter.*—1.0 cm.
*Color.*—Near RHS Greyed-Orange N170D.
*Orientation.*—Approximately 15 to 45° from stem.
*Strength.*—Very strong.
*Texture.*—Villous, moderately dense.
Sepals:
*Shape.*—Quantity per flower: Average 10.
*Length.*—Approximately shortest: Average 1.8 cm longest: 3.9 cm.
*Width.*—Approximately 0.6 cm.
*Margin.*—Entire.
*Apex.*—Acute to Cuspidate.
*Texture.*—Glabrous and shiny all surfaces.
*Color, upper surface.*—Near Orange 26B, flushed and streaked Red 53B.
*Color lower surfaces.*—Near RHS Orange 26A.

REPRODUCTIVE ORGANS

Stamens:
*Number.*—Average range 150 to 250.
*Filament length.*—Approximately 0.9 cm.
*Filament color.*—Near RHS Red 53A.
Anthers:
*Shape.*—Oblong.
*Length.*—Approximately 2 mm.
*Color.*—Near RHS Orange-White 159C.
*Pollen.*—Color: Near RHS Yellow-White 158C. Quantity: Moderate.
Pistil:
*Number.*—1.
*Length.*—Approximately 4.0 cm.
*Style.*—Length: Approximately 3.0 cm. Color: Near RHS Orange-Red 31C, base of style near Yellow-Green 153C.
*Stigma.*—Shape: 2 parted, each section folded inward. Size: 5 mm long, 5 mm wide. Color: Near RHS Yellow-Green 144C.
*Ovary.*—Length: 9 mm. Shape: Narrow oblong. Texture: Sericeous, sticky. Color: Near RHS Yellow-Green 145C.

OTHER CHARACTERISTICS

Fruits and seeds: Seed pods ovate, average range 1.3 to 1.9 cm in length, about 5 mm in diameter. Colored near Grey-brown N199A, densely sericeous, hairs near White 155A. Low to moderate seed production, seeds colored near Greyed-Orange 177C.
Temperature tolerance: USDA zones 10 and above.
Disease/pest resistance: More resistant to the pathogen *Bipolaris cactivora* (*Helminthosporium cactivorum*) Neither resistance nor susceptibility to other pathogens or pests of *Echinopsis* observed.
Drought tolerance: Extreme tolerance for drought.

What is claimed is:
1. A new and distinct cultivar of *Echinopsis* plant named 'FLAMBEAU' as herein illustrated and described.

* * * * *